US007978330B2

(12) United States Patent
Reyes, Jr. et al.

(10) Patent No.: US 7,978,330 B2
(45) Date of Patent: Jul. 12, 2011

(54) DETECTING A TARGET USING AN OPTICAL AUGMENTATION SENSOR

(75) Inventors: Hector M. Reyes, Jr., Richardson, TX (US); Mitchell B. Haeri, Irvine, CA (US); Kenneth K. Colson, West Tawakoni, TX (US); Richard A. Cesari, Dallas, TX (US); Timothy G. Brauer, Carrollton, TX (US); Michael C. Menefee, Richardson, TX (US)

(73) Assignee: Raytheon Company, Waltham, MA (US)

(*) Notice: Subject to any disclaimer, the term of this patent is extended or adjusted under 35 U.S.C. 154(b) by 14 days.

(21) Appl. No.: 12/053,665

(22) Filed: Mar. 24, 2008

(65) Prior Publication Data

US 2009/0237668 A1 Sep. 24, 2009

(51) Int. Cl.
*G01N 21/55* (2006.01)
(52) U.S. Cl. ...................................................... 356/445
(58) Field of Classification Search .... 356/237.1–237.5, 356/600–615, 445; 250/152.2, 339.06, 330, 250/342; 398/131, 204, 42, 171
See application file for complete search history.

(56) References Cited

U.S. PATENT DOCUMENTS

| | | | | |
|---|---|---|---|---|
| 3,848,830 A * | 11/1974 | Born | ............................ | 244/3.16 |
| 4,131,791 A | 12/1978 | Lego, Jr. | ....................... | 250/199 |
| 4,234,141 A * | 11/1980 | Miller et al. | ................... | 244/3.13 |
| 4,887,310 A | 12/1989 | Meyzonnette et al. | ....... | 455/604 |
| 5,018,151 A | 5/1991 | Seaton | ............................. | 372/18 |
| 5,449,899 A | 9/1995 | Wilson | | |
| 5,485,012 A | 1/1996 | Liebson | ................... | 250/339.06 |
| 5,644,386 A | 7/1997 | Jenkins et al. | | |
| RE36,393 E | 11/1999 | Glaser-Inbari | ............. | 369/44.23 |
| 6,031,601 A * | 2/2000 | McCusker et al. | ........... | 356/5.01 |
| 6,134,343 A * | 10/2000 | Nichani | ........................ | 382/141 |
| 6,166,803 A | 12/2000 | Milton et al. | .............. | 356/152.2 |
| 6,593,101 B2 * | 7/2003 | Richards-Kortum et al. | .. | 435/29 |
| 6,665,079 B1 * | 12/2003 | Tocci et al. | .................... | 356/614 |
| 7,224,905 B2 * | 5/2007 | Ruggiero | ...................... | 398/170 |
| 7,282,695 B2 * | 10/2007 | Weber et al. | .................. | 250/225 |
| 7,468,695 B1 * | 12/2008 | Williams | ................. | 342/357.37 |
| 2004/0033472 A1 * | 2/2004 | Varshneya | ....................... | 434/23 |
| 2005/0249377 A1 * | 11/2005 | Fouquet et al. | ............... | 382/103 |
| 2006/0060651 A1 * | 3/2006 | McIntyre et al. | ............. | 235/454 |
| 2007/0034776 A1 | 2/2007 | Weber et al. | | |

OTHER PUBLICATIONS

PCT, Notification of Transmittal of the International Search Report and the Written Opinion of the International Searching Authority, or the Declaration, International Application No. PCT/US2009/035647, 12 pages, Feb. 18, 2010.

* cited by examiner

*Primary Examiner* — Hoa Q. Pham
*Assistant Examiner* — Isiaka O Akanbi
(74) *Attorney, Agent, or Firm* — Baker Botts L.L.P.

(57) ABSTRACT

In one embodiment, detecting a target includes directing a laser beam towards an area and detecting the laser beam reflected from the area. Whether the received laser beam comprises an optically augmented reflection indicating retroreflection from a target is determined. The target indicates presence of an explosive device. The target is detected if the received laser beam comprises the optically augmented reflection.

21 Claims, 4 Drawing Sheets

DETECTING A TARGET USING AN OPTICAL AUGMENTATION SENSOR

TECHNICAL FIELD

This invention relates generally to the field of detection systems and more specifically to detecting a target using an optical augmentation sensor.

BACKGROUND

Detection systems may be used to detect hazardous objects. For example, military personnel may use a detection system to detect bombs in enemy territory. Detection systems should detect hazardous objects in an efficient and effective manner. In certain situations, however, known detection systems fail to do so.

SUMMARY OF THE DISCLOSURE

In accordance with the present invention, disadvantages and problems associated with previous techniques for detecting targets may be reduced or eliminated.

According to one embodiment of the present invention, detecting a target includes directing a laser beam towards an area and detecting the laser beam reflected from the area. Whether the received laser beam comprises an optically augmented reflection indicating retro-reflection from a target is determined. The target indicates presence of an explosive device. The target is detected if the received laser beam comprises the optically augmented reflection.

Certain embodiments of the invention may provide one or more technical advantages. A technical advantage of one embodiment may be that a target is detected using a laser beam that is retro-reflected from the target. Retro-reflection may effectively and efficiently detect targets such as optical/electro-optical (O/EO) devices. Another technical advantage of one embodiment may be that the target may indicate the presence of an explosive device. That is, the target need not be the explosive device itself, but may be an O/EO device, for example, binoculars, that may be associated with personnel planting an explosive device.

Certain embodiments of the invention may include none, some, or all of the above technical advantages. One or more other technical advantages may be readily apparent to one skilled in the art from the figures, descriptions, and claims included herein.

BRIEF DESCRIPTION OF THE DRAWINGS

For a more complete understanding of the present invention and its features and advantages, reference is now made to the following description, taken in conjunction with the accompanying drawings, in which.

DETAILED DESCRIPTION OF THE DRAWINGS

Embodiments of the present invention and its advantages are best understood by referring to FIGS. 1 through 6 of the drawings, like numerals being used for like and corresponding parts of the various drawings.

Figure 1:
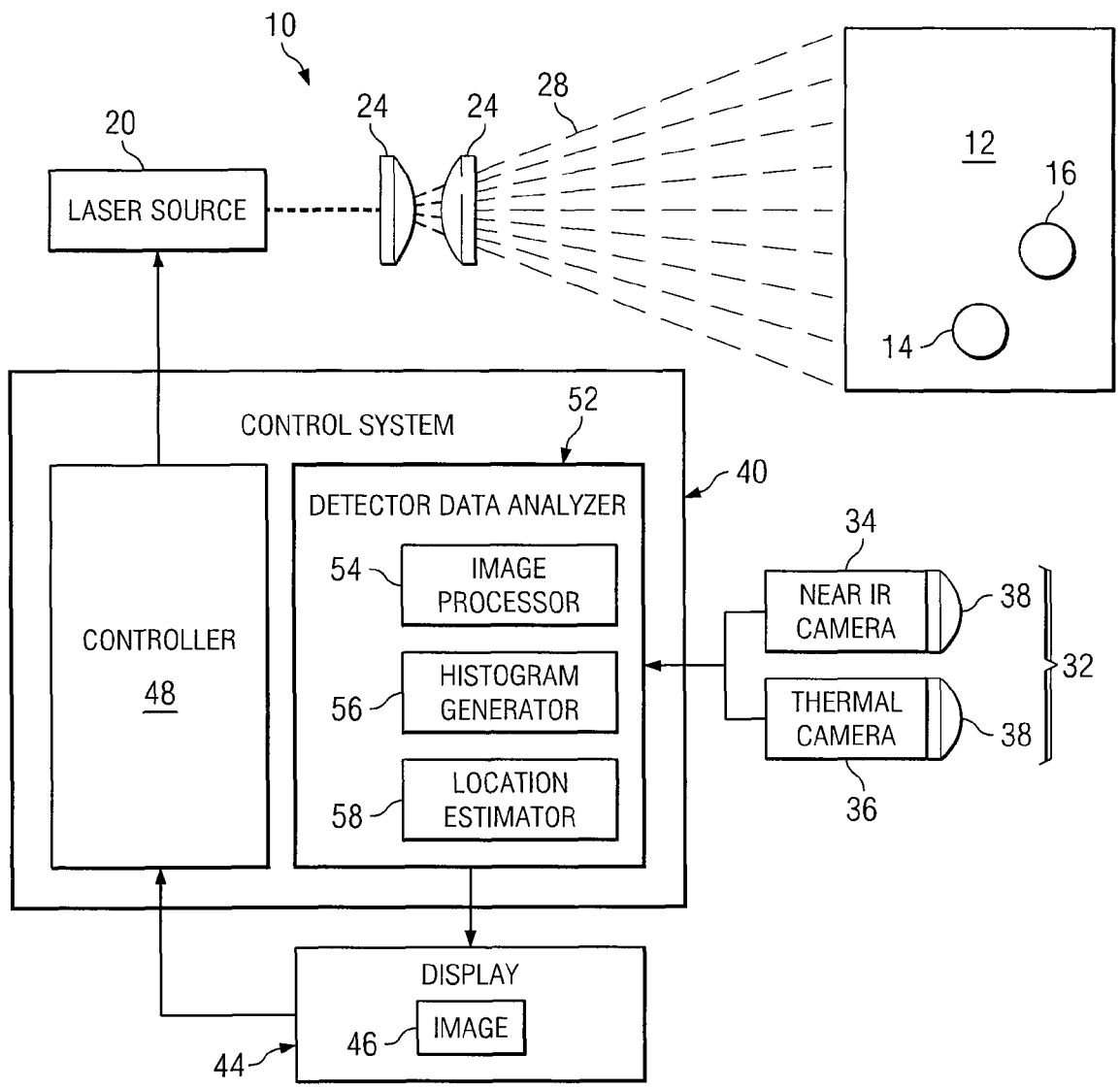
FIG. 1 illustrates an example of an optical augmentation (OA) sensor system operable to detect a target in an area.

FIG. 1 illustrates an example of an optical augmentation (OA) sensor system 10 operable to detect a target 14. OA sensor system 10 detects target 14 using a laser beam 28 that is retro-reflected from target 14. Target 14 may indicate the presence of an explosive device 16.

In the illustrated embodiment, area 12 represents an area that may be scanned by OA sensor system 10. For example, area 12 represents an indoor or outdoor scene that includes one or more objects that can reflect laser beam 28. Examples of area 12 include an airport, a residential or business building, wartime territory, and/or other suitable area.

Target 14 indicates the presence of an explosive device, and may represent an optical or electro-optical (O/EO) device that a person with explosive device 16 may use. Examples of target 14 include binoculars, telescopes, camcorders, cameras, or other suitable O/EO device. An O/EO device typically includes an aperture, optics, and a focal plane. The aperture allows light to enter the device. Optics focus the light and may include one or more lenses. The light forms an image at the focal plane.

Explosive device 16 represents a device that includes an explosive charge, a detonator, and/or an initiation system, and is typically designed to destroy or incapacitate personnel or vehicles. For example, explosive device 16 may represent an improvised explosive device (IED). An explosive device may include other destructive, lethal, noxious, pyrotechnic, or incendiary material. For example, an explosive device may include shrapnel such as nails or ball bearings.

OA sensor 10 includes a laser source 20, a beam spoiler 24, detectors 32, a control system 40, and a display 44. Laser source 20 generates a laser beam 28. Examples of laser source 20 include a laser designator, a Multiple Integrated Laser Engagement System (MILES), a gas continuous wave laser generator (such as a helium neon (HeNe) laser generator), and/or other suitable laser generator. A dispersive optic (such as a lens, holographic diffuser, or other dispersive optic) may illuminate the field of view of detectors 22. Beam spoiler 24 filters higher order components of laser beam 28.

Laser source 20 may be modulated at, for example, approximately one-half the frame rate of detectors 22. Modulating laser source 20 may increase the signal-to-noise ratio of the return from target 14. The modulation may allow system 10 to reject transient signals (such as clutter) that do not oscillate according to the transmitted modulation. A tone detection and threshold operation can be accomplished using any suitable technique, such as single-frequency tone detection and Fourier analysis.

Laser beam 28 may have any suitable wavelength, for example, a wavelength of approximately 0.8 micrometers (μm) to 1.6 μm, for example approximately 0.86, 0.90, 1.1, or 1.5 μm. Laser beam 28 may have any suitable divergence, for example, a divergence in the range of less than 10 millirads, for example, less than 8, 7, 2, 1, or 0.5 millirads or less than 200 microrads.

Laser beam 28 can retro-reflect from target 14 comprising an O/EO device. For example, laser beam 28 passes through the aperture of the O/EO device. A reflective area of the device, such as focal plane, reflects laser beam 28. Optics of the device optically augments the reflected laser beam 28. Laser beam 28 retro-reflected from target 14 yields a particular laser signature that identifies target 14.

Detectors 32 detect laser beam 28 reflected from area 12, which may include laser beam 28 retro-reflected from target 14. A detector 32 may be a camera such as charge-coupled device (CCD) camera. Detectors 32 may detect any suitable wavelengths, for example, infrared, visible, or ultraviolet wavelengths. A detector 32 may have a filter 38 that filters light to select wavelengths that enter detector 32. Detector 32 may have a bandpass filter that reduces ambient illumination in non-illuminated spectral bands.

In one embodiment, a camera may have a field of view of 20 degrees or less. The camera may be disposed on a movement system that points the camera in different directions. Examples of movement systems include gimbal and pan/tilt platforms.

In one embodiment, detectors 32 include a detection camera and an interrogation camera. The detection camera is used first for wide area detection. If a suspicious target 14 is detected by the detection camera, the interrogation camera is used to detect human activity near target 14. In the illustrated embodiment, near-infrared (near-IR) camera 34 operates as the detection camera, and thermal camera 36 operates as the interrogation camera.

In one embodiment, the wavelengths of laser beam 28 may be selected and/or set to match the wavelengths detectable by detectors 32. For example, a wavelength between 600 nanometers and 1 micron, for example, approximately 900 nanometers may be used with a charge-coupled device (CCD) camera. A wavelength between 8 and 12 microns, for example, approximately 10 microns may be used with a thermal camera. In one embodiment, detectors 32 may be selected and/or set to detect the wavelength of laser beam 28. In one embodiment, detectors 32 may have boresights with fields of view that match the beam divergence of laser beam 28.

Control system 40 includes a controller 48, and a detector data processor 52. GUI 44 receives input (such as commands) from a user, and reports output to the user. Controller 48 controls the operation of laser source 20 and/or detectors 32, and may do so in response to commands from GUI 44. Controller 48 may control the wavelength and/or beam divergence of laser beam 28. Controller 48 may also control the wavelength detected by detectors 32 and/or the azimuth (AZ) and/or elevation (EL) angles of detectors 32.

Detector data analyzer 52 analyzes data received from detectors 32. Detector data analyzer 52 includes an image processor 54, a histogram generator 56, and a location estimator 58. Image processor 54 generates image data from detector signals from one or more detectors 32. The image data is then sent to display 44 to generate an image 46 representing area 12. Display may comprise a display of a computer. Image 46 may include a portion that represents target 14.

Histogram generator 56 generates a histogram that represents image 46. A histogram may record frequency counts at each grayscale value of image 46. For example, for each grayscale value, the histogram may record the number of pixels that have that value. An example of a histogram is described in more detail with reference to FIG. 2. The laser signature of target 14 may manifest itself in a histogram.

Location estimator 58 estimates the location of target 14 from the detector signals. Location estimator 58 may estimate the location in any suitable manner. For example, location estimator 58 may estimate the distance from the intensity of reflected laser beam 28, and the angle from the AZ/EL angle of reflected laser beam 28.

A component of system 10 may include an interface, logic, memory, and/or other suitable element. An interface receives input, sends output, processes the input and/or output, and/or performs other suitable operation. An interface may comprise hardware and/or software.

Logic performs the operations of the component, for example, executes instructions to generate output from input. Logic may include hardware, software, and/or other logic, and may be stored in computer-readable storage medium. Certain logic, such as a processor, may manage the operation of a component. Examples of a processor include one or more computers, one or more microprocessors, one or more applications, and/or other logic.

A memory stores information. A memory may comprise computer memory (for example, Random Access Memory (RAM) or Read Only Memory (ROM)), mass storage media (for example, a hard disk), removable storage media (for example, a Compact Disk (CD) or a Digital Video Disk (DVD)), database and/or network storage (for example, a server), and/or other computer-readable medium.

Modifications, additions, or omissions may be made to system 10 without departing from the scope of the invention. The components of system 10 may be integrated or separated. Moreover, the operations of system 10 may be performed by more, fewer, or other components. For example, the operations of controller 48 and detector data processor 52 may be performed by one component, or the operations of GUI 44 may be performed by more than one component. Additionally, operations of system 10 may be performed using any suitable logic comprising software, hardware, and/or other logic. As used in this document, "each" refers to each member of a set or each member of a subset of a set.

Figure 2:
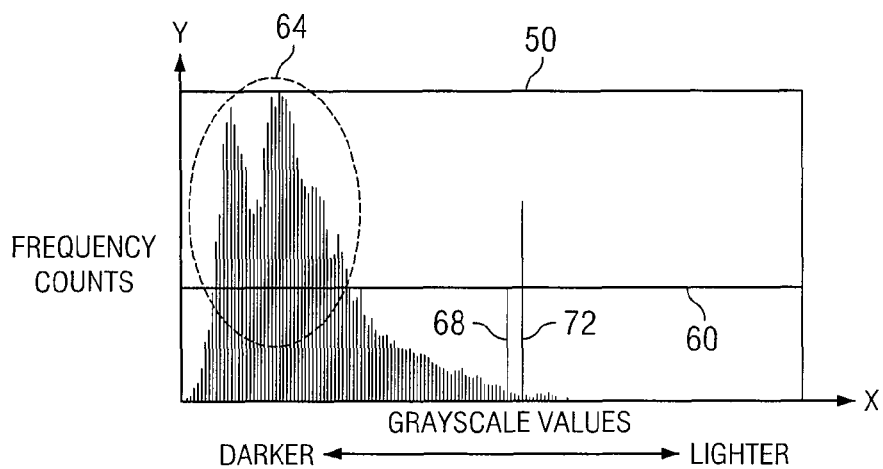
FIG. 2 illustrates an example of a histogram that may be generated by the OA sensor system of FIG. 1.

FIG. 2 illustrates an example of a histogram 50 of area 12. In the illustrated embodiment, the x-axis represents grayscale values, and the y-axis represents frequency counts of a particular grayscale value, such as the number of pixels that have the value.

Threshold 60 represents a minimum frequency count that is associated with beam 28 retro-reflected from target 14 and detected by a detector 32 as an optically augmented (OA) return. A frequency count above threshold 60 is designated as an OA return, and may indicate the presence of target 14.

Histogram 50 includes frequency counts that represent background 64, glints 68, and an OA return 72. Background counts 64 represent the background, and may typically be towards the darker end of the grayscale. Glints 62 may be towards the lighter end of the grayscale, and may be under threshold 60. OA returns 72 are typically towards the lighter end of the grayscale and exceed threshold 60.

Figure 3:
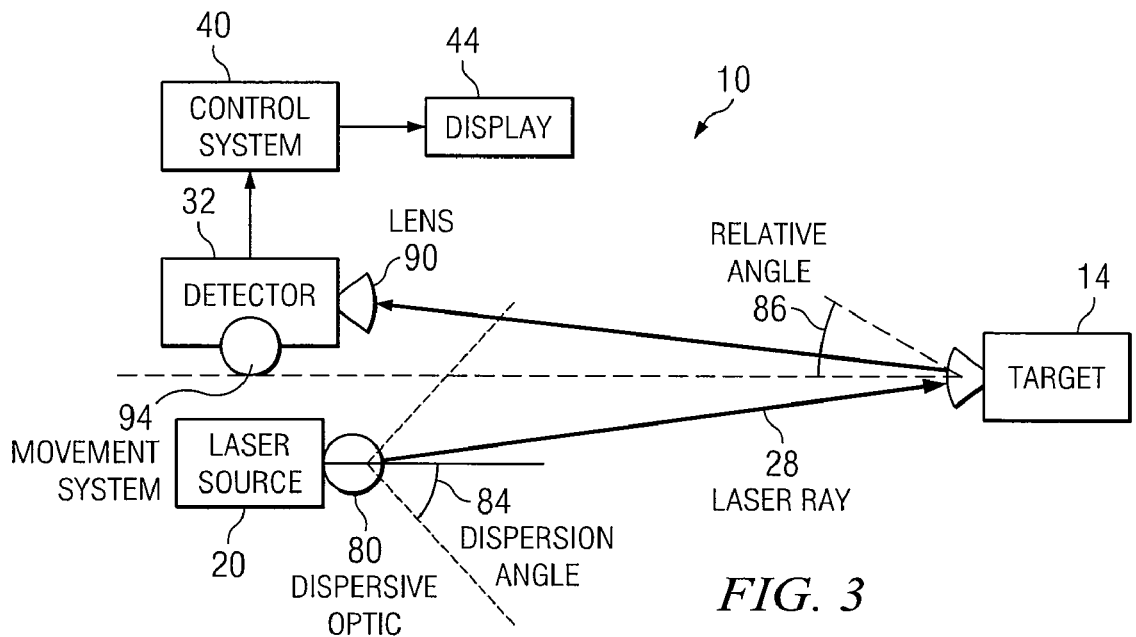
FIG. 3 illustrates another example of an OA sensor system operable to detect a target in an area.

FIG. 3 illustrates another example of an OA sensor system 10 operable to detect target 14. OA sensor 10 includes laser source 20, detector 32, control system 40, and display 44 coupled as shown.

In the illustrated example, laser source 20 includes a dispersive optic 80 that disperses laser beam 28 through a dispersion angle 84 measured from the axis of dispersive optic 80. Examples of dispersive optic 80 include a lens, holographic diffuser, or other dispersive optic. Target 14 can reflect light beam 28 received with a relative angel 86 measured from the lens axis of target 14.

In the illustrated example, detector 32 includes a lens 90 and a movement system 94. Lens focuses light towards detector 32. Movement system 94 moves detector 32 and/or laser source 20 to point detector 32 and/or laser source 20 in different directions. Examples of movement system 94 include gimbal and pan/tilt platforms.

Figure 4:
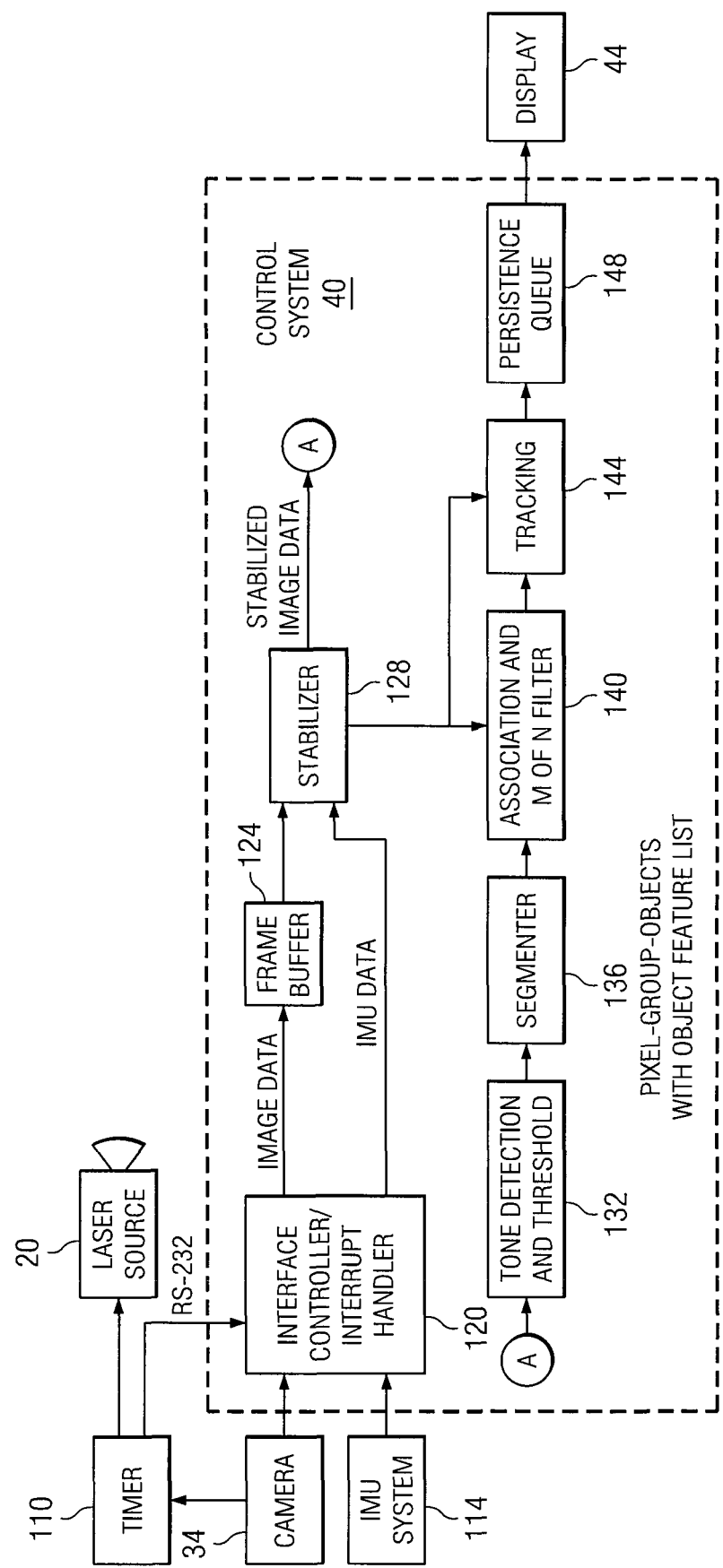
FIG. 4 illustrates an example of a control system that may be used with an OA sensor system.

FIG. 4 illustrates an example of a control system 40 that may be used with an OA sensor system 10. In the illustrated embodiment, OA sensor 10 includes laser source 20, a timer 110, camera 34, an Inertial Measurement Unit (IMU) system 114, control system 40, and display 44 coupled as shown.

In the illustrated embodiment, timer 110 is used to modulate laser source 20. Laser source 20 may be modulated in any suitable manner. An example of modulation is described with reference to FIG. 5. IMU system 114 establishes orientation angles of camera 34 that describe the rotation of camera 34 with respect to the ground.

In the illustrated embodiment, control system 40 includes an interface controller/interrupt handler 120, a frame buffer 124, a stabilizer 128, a tone detection and threshold 132, a segmenter 136, an association and M of N filter 140, a tracking module 144, and a persistence queue 148.

Interface controller/interrupt handler 120 receives timing signals from timer 110, image signals from camera 34, and IMU signals from IMU system 114. Interface controller/interrupt handler 120 sends image data generated from the image signals to frame buffer 124, and sends IMU data generated from the IMU signals to stabilizer 128. Frame buffer 124 buffers the image data.

Stabilizer 128 stabilizes the image data with respect to the ground according to the IMU data. Stabilizer 128 sends the stabilized image data to tone detection and threshold 132, association and M of N filter 140, and/or tracking module 144.

Tone detection and threshold 132 may filter the image data for reflections oscillating at the same frequency as the transmitted source, and may reject weak or off-frequency oscillations that do not meet a specified threshold. Segmenter 136 segments the detected targets in the image data into image data points (pixels) for output to the association and M of N filter. Association and M of N filter 140 merges individual image data point (pixels) into target detections. Tracking module 144 tracks target detections across multiple sets of image data. Persistence queue 148 discards tracks that have not been observed within a certain number of recent frames.

Figure 5:
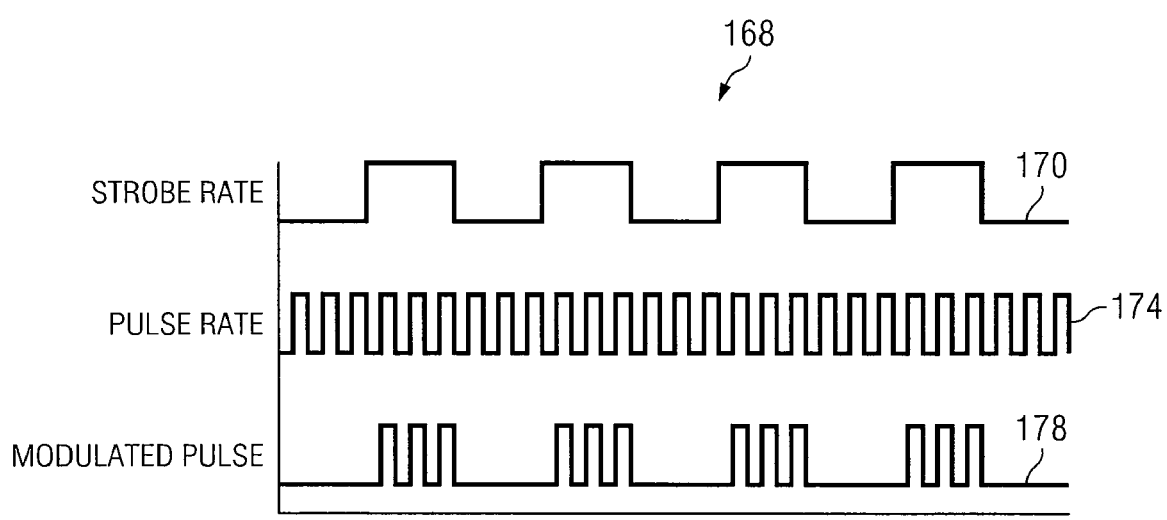
FIG. 5 is a graph illustrating an example of the modulation of the laser beam from the laser source.

FIG. 5 is a graph 168 illustrating an example of modulation of laser beam 28. Graph 168 includes a strobe rate 170, a pulse rate 174, and a modulated pulse 178. Strobe rate 170 specifies the frames during which the laser fires. Tone Detection and Threshold 132 knows the strobe waveform. Pulse rate 174 is a continuous modulation synchronized to the detector frame rate. Modulated pulse 178 is the waveform that directly controls the laser firing circuitry.

Figure 6:
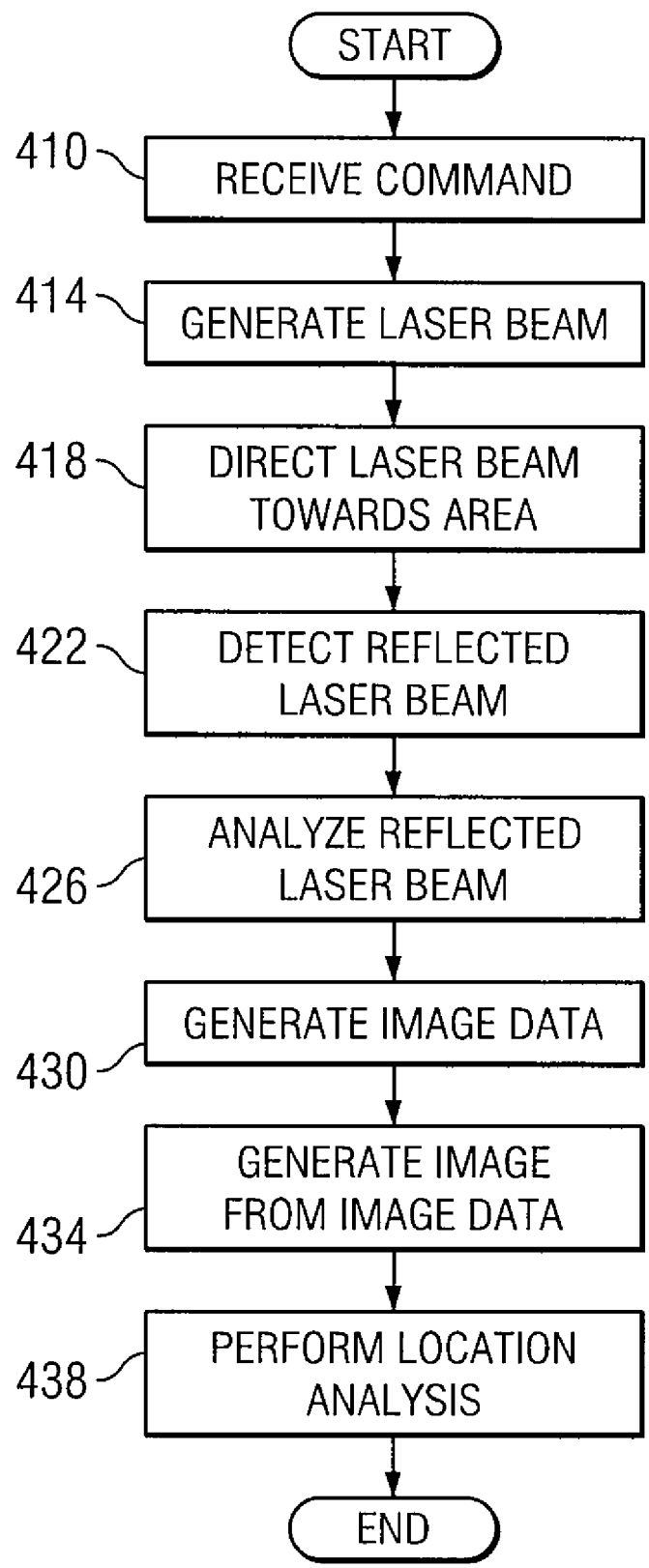
FIG. 6 illustrates an example of a method of detecting a target that may be used by the OA sensor system of FIG. 1.

FIG. 6 illustrates an example of a method of detecting target 14 with OA sensor system 10. In the method, controller 48 receives a command at step 410 to enter an OA mode. The command may be input by user through GUI 44. In the OA mode, controller 48 sets laser source 20 to generate laser beam 28 with a large beam divergence to allow for a wide-area search to be performed. Laser source generates laser beam 28 at step 414. Beam spoiler 24 directs laser beam 28 towards area 12 at step 418. Area 12 including target 14 reflects laser beam 28.

Detectors 32 detect reflected laser beam 28 at step 422. Detector data analyzer 52 analyzes the reflected beam 28 at step 426. Histogram generator 56 may generate a histogram 50 representing an image of scene 12 to determine whether histogram 50 includes a signature of target 14, such as a frequency count that exceeds a particular threshold.

Image processor 54 generates image data at step 430. GUI 44 generates an image from the image data at step 434. Location estimator 58 performs a location analysis at step 438. The location may be reported through GUI 44 in the form of GPS coordinates. After the location analysis, the method terminates.

Modifications, additions, or omissions may be made to the method without departing from the scope of the invention. The method may include more, fewer, or other steps. Additionally, steps may be performed in any suitable order.

Certain embodiments of the invention may provide one or more technical advantages. A technical advantage of one embodiment may be that a target is detected using a laser beam that is retro-reflected from the target. Retro-reflection may effectively and efficiently detect targets such as optical/electro-optical (O/EO) devices. Another technical advantage of one embodiment may be that the target may indicate the presence of an explosive device. That is, the target need not be the explosive device itself, but may be an O/EO device, for example, binoculars, that may be associated with personnel planting an explosive device.

Although this disclosure has been described in terms of certain embodiments, alterations and permutations of the embodiments will be apparent to those skilled in the art. Accordingly, the above description of the embodiments does not constrain this disclosure. Other changes, substitutions, and alterations are possible without departing from the spirit and scope of this disclosure, as defined by the following claims.

What is claimed is:

1. A method for detecting a target, comprising:
   directing a laser beam towards an area;
   detecting, by a detector, the laser beam reflected from the area;
   determining, by a control system, whether the received laser beam comprises an optically augmented reflection indicating retro-reflection optically augmented by a target, the target indicating presence of an explosive device, the determining comprising:
      receiving an orientation angle of the detector with respect to the ground;
      generating an image of the detected laser beam according to the received orientation angle of the detector with respect to the ground;
      generating a histogram from at least the image representing a plurality of grayscale values of the area, the histogram comprising a frequency count for each grayscale value; and
      determining that a particular frequency count of the histogram is greater than a threshold;
   detecting the target if the received laser beam comprises the optically augmented reflection; and
   estimating a location of the target according to an intensity and an angle of the detected laser beam, the location comprising Global Positioning Satellite (GPS) coordinates of the target.

2. The method of claim 1, wherein the laser beam is retro-reflected from the target by:
   reflecting the laser beam from a reflective area of the target; and
   optically augmenting the laser beam using optics of the target.

3. The method of claim 1, further comprising:
   adjusting a wavelength of the laser beam directed towards the area.

4. The method of claim 1, further comprising:
   adjusting a beam divergence of the laser beam directed towards the area.

5. The method of claim 1, further comprising:
adjusting a wavelength detectable by a detector operable to detect the laser beam.

6. The method of claim 1, wherein detecting the laser beam reflected from the area further comprises:
detecting the laser beam using a camera.

7. The method of claim 1, wherein determining whether the received laser beam comprises the optically augmented reflection further comprises:
establishing a plurality of frequency counts for a plurality of grayscale values of the area; and
determining that there is the optically augmented reflection from the plurality of frequency counts.

8. The method of claim 1, wherein determining whether the received laser beam comprises the optically augmented reflection further comprises:
generating a histogram representing a plurality of grayscale values of the area, the histogram comprising a frequency count for each grayscale value;
determining that a frequency count of the histogram is greater than a threshold; and
determining that there is the optically augmented reflection.

9. The method of claim 1, further comprising:
detecting the laser beam reflected from the area using a thermal camera.

10. The method of claim 1, further comprising:
estimating a location of the target according to the detected laser beam.

11. A system for detecting a target, comprising:
a laser source operable to:
generate a laser beam directed towards an area;
one or more detectors operable to:
detect the laser beam reflected from the area; and
a control system operable to:
determine whether the received laser beam comprises an optically augmented reflection indicating retro-reflection optically augmented by a target, the target indicating presence of an explosive device, the determining comprising:
receiving an orientation angle of a detector of the one or more detectors with respect to the ground;
generating an image of the detected laser beam according to the received orientation angle of the detector with respect to the ground;
generating a histogram from at least the image representing a plurality of grayscale values of the area, the histogram comprising a frequency count for each grayscale value; and
determining that a particular frequency count of the histogram is greater than a threshold; and
detect the target if the received laser beam comprises the optically augmented reflection; and
estimate a location of the target according to an intensity and an angle of the detected laser beam, the location comprising Global Positioning Satellite (GPS) coordinates of the target.

12. The system of claim 11, wherein the laser beam is retro-reflected from the target by:
reflecting the laser beam from a reflective area of the target; and
optically augmenting the laser beam using optics of the target.

13. The system of claim 11, the control system further operable to:
adjust a wavelength of the laser beam directed towards the area.

14. The system of claim 11, the control system further operable to:
adjust a beam divergence of the laser beam directed towards the area.

15. The system of claim 11, the control system further operable to:
adjust a wavelength detectable by a detector of the one or more detectors.

16. The system of claim 11, the control system further operable to determine whether the received laser beam comprises the optically augmented reflection by:
establishing a plurality of frequency counts for a plurality of grayscale values of the area; and
determining that there is the optically augmented reflection from the plurality of frequency counts.

17. The system of claim 11, the control system further operable to determine whether the received laser beam comprises the optically augmented reflection by:
generating a histogram representing a plurality of grayscale values of the area, the histogram comprising a frequency count for each grayscale value;
determining that a frequency count of the histogram is greater than a threshold; and
determining that there is the optically augmented reflection.

18. The system of claim 11, the one or more detectors comprising a thermal camera.

19. The system of claim 11, the control system further operable to:
estimate a location of the target according to the detected laser beam.

20. The system of claim 11, further comprising a movement system operable to move a detector of the one or more detectors.

21. A system for detecting a target, comprising:
means for directing a laser beam towards an area;
means for detecting the laser beam reflected from the area;
means for determining whether the received laser beam comprises an optically augmented reflection indicating retro-reflection optically augmented by a target, the target indicating presence of an explosive device, the determining comprising:
receiving an orientation angle of the means for detecting with respect to the ground;
generating an image of the detected laser beam according to the received orientation angle of the detector with respect to the ground;
generating a histogram from at least the image representing a plurality of grayscale values of the area, the histogram comprising a frequency count for each grayscale value; and
determining that a particular frequency count of the histogram is greater than a threshold; and
means for detecting the target if the received laser beam comprises the optically augmented reflection; and
means for estimating a location of the target according to an intensity and an angle of the detected laser beam, the location comprising Global Positioning Satellite (GPS) coordinates of the target.

* * * * *